United States Patent [19]

Staub et al.

[11] Patent Number: 5,713,936
[45] Date of Patent: Feb. 3, 1998

[54] IMPLANTABLE MEDICAL DEVICE WITH END-OF-LIFE BATTERY DETECTION CIRCUIT

[75] Inventors: Roland Staub; Gerd Fehrmann, both of Pirna; Rüdiger Wolf, Rabenau; Thomas Fischer; Hartmut Heimer, both of Pirna, all of Germany

[73] Assignee: Litronik Batterietechnologie GmbH & Co., Pirna, Germany

[21] Appl. No.: 590,143

[22] Filed: Jan. 23, 1996

[30] Foreign Application Priority Data

Nov. 8, 1995 [EP] European Pat. Off. ............ 95250273

[51] Int. Cl.$^6$ ..................... A61N 1/378; G01N 27/416
[52] U.S. Cl. .................... 607/29; 324/434; 324/433
[58] Field of Search ................. 607/27, 29, 34; 324/433, 434, 450, 426

[56] References Cited

U.S. PATENT DOCUMENTS

| 3,303,488 | 2/1967 | Anderson | 324/450 |
|---|---|---|---|
| 3,746,005 | 7/1973 | Thaler et al. | 607/29 |
| 3,757,793 | 9/1973 | Fester et al. | 607/27 |
| 3,757,795 | 9/1973 | Anderson | 607/12 |
| 4,424,491 | 1/1984 | Bobbett et al. | 324/434 |
| 4,445,090 | 4/1984 | Melocik et al. | 324/433 |
| 4,543,304 | 9/1985 | DeHaan | 429/91 |
| 4,839,633 | 6/1989 | Krenik | 324/434 |
| 5,045,163 | 9/1991 | Nyberg et al. | 324/450 |
| 5,137,020 | 8/1992 | Wayne et al. | 607/29 |
| 5,302,902 | 4/1994 | Groehl | 324/434 |

*Primary Examiner*—William E. Kamm
*Assistant Examiner*—Carl H. Layno
*Attorney, Agent, or Firm*—Spencer & Frank

[57] ABSTRACT

A battery-operated implantable medical device comprises a battery, a measuring device for determining the state of charge of the battery through measurement of the no-load voltage, and an electric load. The no-load voltage of the battery has an increased drop in a range in which a remaining residual energy suffices to keep the operation of the device going for a minimum period of time required to carry out a therapeutic process.

16 Claims, 4 Drawing Sheets

IMPLANTABLE MEDICAL DEVICE WITH END-OF-LIFE BATTERY DETECTION CIRCUIT

BACKGROUND OF THE INVENTION

The invention relates to a battery-operated, implantable medical device having a battery, a measuring means for determining the state of charge of the battery by measuring the no-load voltage, and an electric load, wherein the no-load voltage of the battery has an increase drop-off in a range in which a remaining residual energy is sufficient to maintain operation of the medical device for carrying out a therapeutic process.

Battery-operated implantable medical devices which have a measuring means for determining the charge condition of the battery are known.

U.S. Pat. No. 3,757,793 discloses a cardiac pacemaker operated by a battery, in which the state of charge of the battery is determined through measurement of the no-load voltage. Here, the no-load voltage decreases gradually during discharge until it reaches zero.

At the beginning of the discharge, the known battery has a range with a high initial voltage. After the battery has discharged about 10% of the total energy, the no-load voltage drops almost at once to the operating voltage. At this level the no-load voltage remains approximately constant until the battery has discharged about 90% of its total energy. The no-load voltage then drops at once to a terminal voltage which is clearly below the operating voltage but sufficient for operating the device. This terminal voltage remains more or less constant until the battery has lost all its utilisable residual energy. Then, again almost at once, the no-load voltage drops to zero.

The known battery makes it possible to ascertain the state of charge of the battery in a simple manner. To achieve this, the open circuit voltage OCV is measured and compared to the values of the initial, the operating and the terminal voltages.

This ensures that only fully charged batteries are implanted.

Furthermore, it is possible to ascertain whether the service life of the battery is just about coming to an end at a time when the remaining residual energy still suffices to keep the operation going for the minimum period of time required to carry out a therapeutic process. During this period, the battery may, for example, be exchanged. Since the service life of the battery may be reliably predicted and hence no back up supplies are required, it is possible to make use of almost the entire energy of the battery.

The known arrangement, however, poses a problem.

In order to measure the no-load voltage and to determine the state of charge from the voltage measured, an electronic circuit is necessary, at least in the implanted state. This circuit, however, usually requires a symmetrical voltage supply. Therefore, a voltage supply is needed which delivers a reference potential and two different polarities based on the reference potential. The known arrangement, however, is not able to provide this.

SUMMARY OF THE INVENTION

The invention therefore, has, in particular, the object of providing a battery-operated, implantable medical device in which the battery ensures both the voltage supply for an electric load and also the symmetrical voltage supply for a measuring means used for determining the state of charge of the battery. In view of the fact that the device is implanted into the human body, the additional constructional expenditure required for this must, moreover, be as low as possible with regard to the increase in weight and dimensions.

This object is achieved by provision of a battery-operated implantable medical device as first described above wherein: the battery includes a plurality of cells connected in a series circuit, a first voltage pick-up is arranged on a free anode of the battery for picking up a first potential and a second voltage pick-up is arranged on a free cathode of the battery for picking up a second potential, the electric load is electrically conductively coupled to the first and second voltage pick-ups to be energized by a total voltage drop across the battery, a third voltage pick-up is arranged on an electrode positioned between the free anode and free cathode in the series circuit in order to pick-up a reference potential and to energize the measuring device with a symmetrical voltage supply, the measuring device includes a measuring circuit comprising at least one of a level transducer and an adding means, the measuring device being electrically conductively coupled at its inputs to the first and second voltage pick-ups for measuring the total voltage drop across the battery, the measuring device further includes a threshold value member with at least one threshold value coupled to an input of the measuring circuit for generating a battery conditioned signal, the measuring circuit and the threshold value member each has an input for a reference point which is electrically conductively coupled to the third voltage pick-up, and the measuring circuit and the threshold value member are each electrically conductively coupled to the first and second voltage pick-ups to be energized with a voltage in symmetry with the third voltage pick-up.

The invention is based on the technical teaching that a battery has a series circuit of several cells with three voltage taps forming a symmetrical voltage system, and that a measuring means supplied by the symmetrical voltage system evaluates the maximum voltage occurring between the three voltage taps.

The arrangement according to the invention mainly consists of a battery, a measuring means for determining the state of charge of the battery and an electric load, for example the pulse generator of a cardiac pacer.

Like the battery disclosed in U.S. Pat. No. 3,757,793 the battery provided in the arrangement according to the invention emits graduated discrete voltage values, depending on the remaining residual energy.

The battery has a series connection of several cells, the voltages of the individual cells being thereby added together. The distance between these discrete voltage values of the battery, therefore, also increases which makes it easier to distinguish these discrete voltage values and thus to determine the state of charge.

The series connection has a free anode and a free cathode. The free anode has a first voltage tap and the free cathode has a second voltage tap, so that a first and a second potential, and thus the total voltage drop in the battery, may be picked up.

To supply the voltage, the electric load is connected to the first and second voltage tap and can therefore use the total voltage drop in the battery as supply voltage.

A third voltage tap is provided on another cell positioned in the series connection in between the outer cells. The potential of this third voltage tap lies between the potential of the first and the second voltage tap and serves as a reference potential. This produces a symmetrical voltage system to supply voltage to the measuring means.

The measuring means evaluates the battery voltage and produces a signal according to the state of charge of the battery. For this, the measuring means measures the total decrease in the voltage drop across the battery and compares the voltage measured with the discrete voltage values which reflect the condition of the battery.

Thus, the arrangement according to the invention achieves three main objectives.

Firstly, the total voltage drop across the battery is available to the electric load.

Secondly, a symmetrical voltage system is available for supplying the measuring means.

Thirdly, the measuring means evaluates the total voltage drop across the battery, thereby achieving the greatest possible accuracy.

As the accuracy of the measuring means increases, the requirements as to the distance between the discrete voltage values become less. When the accuracy of the measuring means is high the discrete voltage values may be close to one another.

This has the advantage of making it possible to position the terminal voltage close to the operating voltage thereby minimising the negative consequences related to the decrease in terminal voltage.

In order to obtain the above step-like voltage curve with several discrete voltage values, a relatively high constructional expenditure with regard to the assembly of the electrodes and the electrolyte, however, is required, but this aim is not entirely compatible with that of maximising the capacity. Due to the fact that the accuracy of the measuring device is increased and therefore the requirements relating to the spacing of the discrete voltage values of the battery are less, the constructional possibilities are advantageously greater.

In a preferred embodiment of the invention, the measuring circuit comprises adding means which adds the voltage between the first potential and the reference potential and between the reference potential and the second potential.

Thus the total voltage drop across the battery is advantageously evaluated.

A threshold value member generates the battery condition signal from the starting signal of the measuring circuit. For this purpose, the threshold value member has one or more threshold values. The battery condition signal is produced as a function of the position of the starting signal of the measuring circuit, relative to the threshold value or values.

In a preferred embodiment of the invention, the threshold value member has three threshold values.

The first threshold value is between the initial voltage and the operating voltage of the battery. When the first threshold value is exceeded, this indicates an almost fully charged battery.

The second threshold value is between the operating voltage and the terminal voltage of the battery. If the initial signal of the measuring circuit is between the first and the second threshold values, the battery is within a normal range of discharge. i.e. though the battery is no longer completely charged, it has sufficiently energy for a reliable operation.

The third threshold value is between the terminal voltage and zero. If the output signal of the measuring circuit is between the second and third threshold values, the battery is in its end phase, just before the complete depletion thereof.

If the third threshold value is not reached, this is an indication of a completely empty battery.

The battery condition signal produced by the threshold value member thus indicates four possible conditions of the state of charge of the battery: full, nearly full, nearly empty and empty.

One variation of the invention provides for a telemetric transfer of the output signal of the measuring circuit or of the battery condition signal to an extracorporeal receiving unit. The measuring device, here, has a transmitter/receiver unit. The transfer may be wireless, for example by means of electromagnetic waves. The reception of the signal is preferably effected by placing an aerial member onto the surface of the body, close to the transmitter unit. This makes it possible to keep the required transmission power and thus the energy consumption of the transmitter at a low level.

In an embodiment of the invention, the transmitter/receiver unit has two modes. In normal operation the transmitter/receiver unit operates as a receiver. If an activation signal is sent by a transmitter positioned outside the body, the transmitter/receiver unit switches over to the transmitting mode and transmits the battery condition signal or the starting signal of the measuring circuit to a receiving unit positioned outside the body. The receiving mode is then reset. This advantageously minimises the energy consumption, since energy is only consumed when actually required, during the transmitting operation, when the consumption is relatively high.

The telemetric transfer enables the monitoring of the condition of a battery of an implanted device in an advantageous manner, without invasive actions being necessary.

In another embodiment of the invention, the electric load has a control unit which evaluates the battery condition signal and controls the consumption of current depending on the state of charge of the battery.

This can, for example, be effected by a cardiac pacer reducing the pulse rate and/or the pulse amplitude when the battery condition signal indicates that the battery is almost empty. This increases the service life of the arrangement.

In another variation of the invention, the housing of the battery is electrically conductively coupled to the third voltage pick-up which is at earth potential. The maximum error voltage occurring in the event of a simple fault in the insulation is thus reduced to half the total voltage of the battery, if the third voltage pick-up is arranged centrally between the first and the second voltage pick-up.

BRIEF DESCRIPTION OF THE DRAWING

Other advantageous further developments of the invention are hereinafter described in greater detail with reference to the drawings which illustrate preferred embodiments of the invention. Shown are.

DETAILED DESCRIPTION OF THE INVENTION

Figure 1:
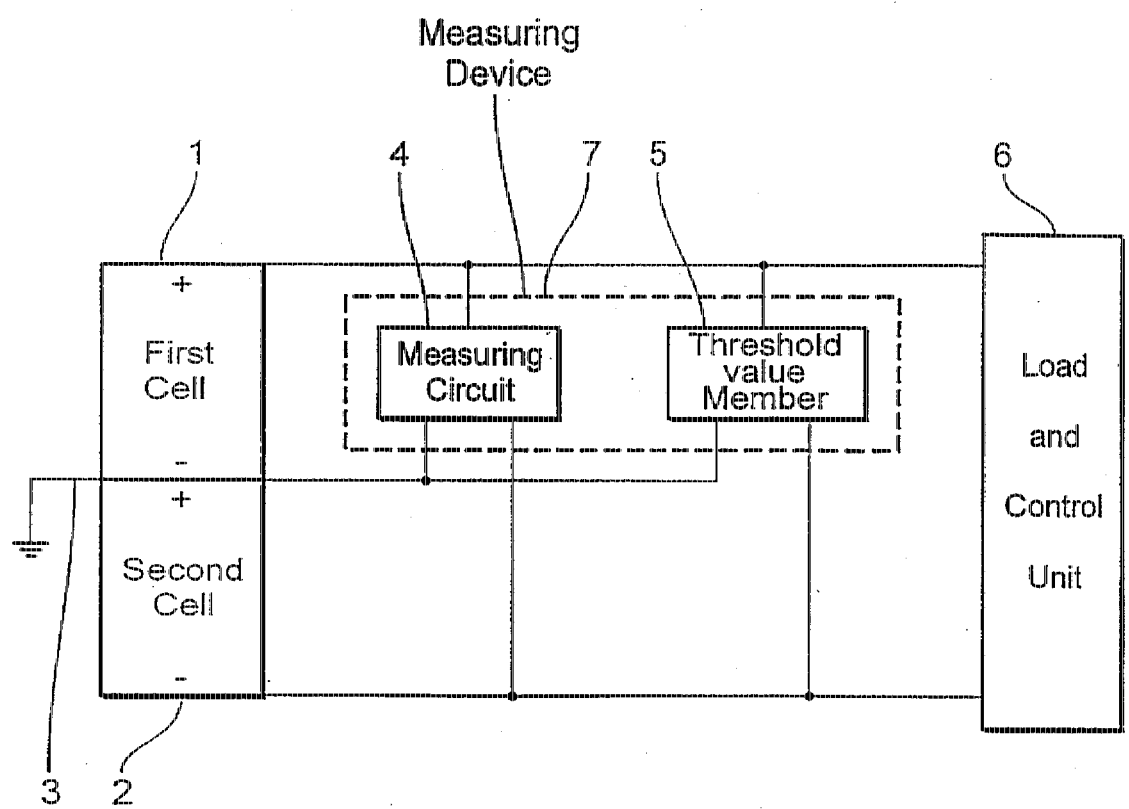
FIG. 1 an embodiment, according to the invention, of an arrangement comprising a battery, a measuring circuit, a threshold value member and an electric load, shown as a block diagram.

The battery has two cells 1, 2 connected in series, the cathode of the first cell 1 and the anode of the second cell 2 being electrically conductively coupled to one another by a connector. A first voltage pick-up is provided on the anode of the first cell 1. A second voltage pick-up is provided on the cathode of the second cell 2. The total voltage drop across the battery may thus be picked up.

A load 6 is electrically conductively coupled to the first and second voltage pick-ups and can thus use the total voltage drop across the battery.

A third voltage pick-up 3 is provided on the connector between cells 1 and 2 from which a reference potential may be picked up. Thus, in combination with the potentials which may be picked up on the first and second voltage pick-ups, there is a symmetrical voltage supply for the measuring device 7.

The third voltage pick-up 3 is coupled to the housing of the battery. The short-circuit voltage occurring in the event of a simple insulation fault is thereby limited to the voltage of the faulty cell 1 or 2 which is about half the amount of the total battery voltage.

The measuring device 7 largely consists of a measuring circuit 4 and a threshold value member 5.

The measuring circuit 4 superimposes cumulatively the change in the first and second potentials, relative to the reference potential, and generates therefrom an output signal which corresponds to a decrease in voltage drop across the entire battery. When the entire voltage drop increases, the output signal also becomes bigger; when the entire voltage drop decreases, the output signal also becomes smaller.

The threshold value member 5 has three threshold values and generates a battery condition signal which depends on the position of the output signal of the measuring circuit, relative to the threshold values. The first threshold value lies between the initial voltage and the operating voltage of the battery; the second threshold value lies between the operating voltage and the terminal voltage and the third threshold value lies between the terminal voltage and zero. If the battery voltage lies above the first threshold value, the battery condition signal indicates a fully charged battery; if the battery voltage drops below the first threshold value, the battery condition signal indicates a full battery; if the battery voltage falls further below the second threshold value, the battery condition signal indicates that the battery is almost empty; if the battery voltage drops below the third threshold value, the battery condition signal indicates, finally, that the battery is completely empty.

Figure 2:
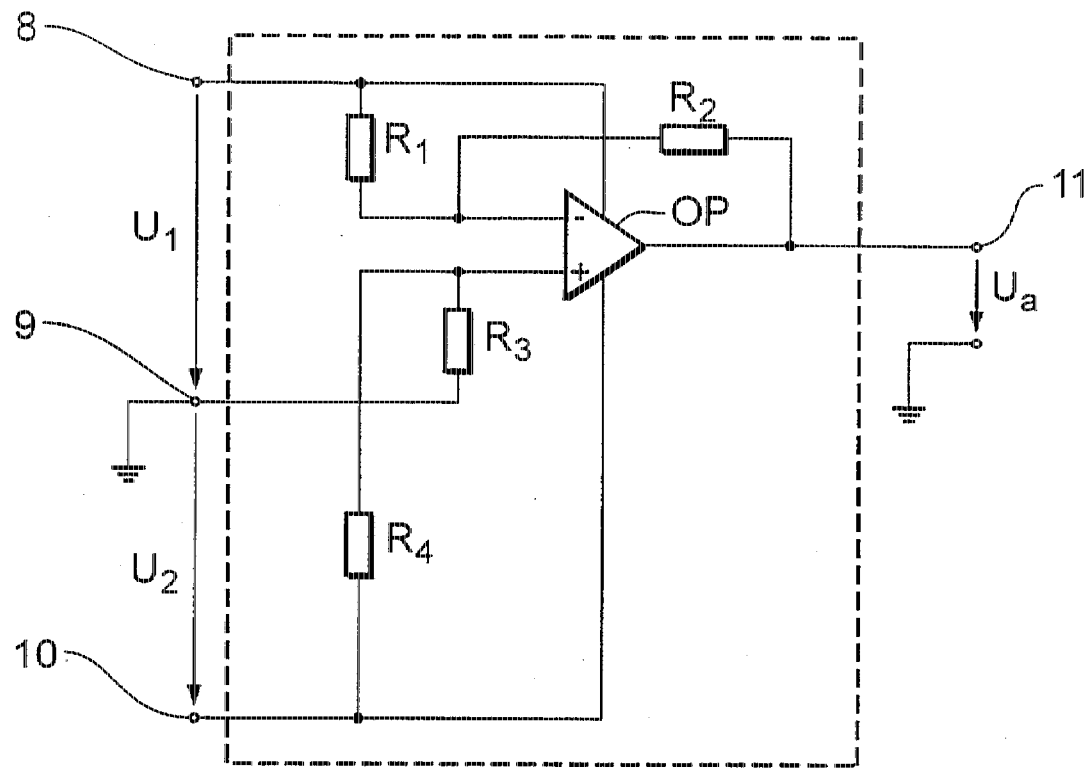
FIG. 2 a circuit diagram of a preferred embodiment of the measuring circuit shown in FIG. 1, FIG. 3 a circuit diagram of another embodiment of the measuring circuit shown in FIG. 1, FIG. 4 a preferred embodiment of the battery shown in FIG. 1, in a detailed, perspective view, and FIG. 5 another embodiment of the battery shown in FIG. 1, in a detailed cross-sectional view.

FIG. 2 shows an embodiment of the measuring circuit 4 illustrated in FIG. 1, in detail as a circuit diagram.

The measuring circuit 4 largely consists of an operational amplifier OP and four resistors $R_1$, $R_2$, $R_3$ and $R_4$.

In the arrangement shown, the operational amplifier operates as a subtracting means which subtracts the voltage $U_1$ from the voltage ($-U_2$), i.e. it is operated here as an adding means.

The voltage $U_1$ is the voltage between the first voltage pick-up 8 and the third voltage pick-up 9 while the voltage $U_2$ is the voltage between the third voltage pick-up 9 and the second voltage pick-up 10. The adding means thus forms the sum of the voltage drops across the two cells and produces an output signal $U_A$, proportional to the total voltage of the battery. The output voltage $U_A$ of the adding means is expressed as follows:

$$U_A = k \cdot (-U_2 - U_1) = -k \cdot (U_1 + U_2) \text{ with } k = \frac{R_2}{R_1}$$

For the proper functioning of the adding means the resistors $R_1$, $R_2$, $R_3$ and $R_4$ must fulfill the coefficient requirement:

$$\frac{R_2}{R_1} = \frac{R_3}{R_4}$$

By varying the amplification factor k the level of the output signal $U_A$ of the measuring circuit 4 may be adapted to the input of the threshold value member 5.

Figure 3:
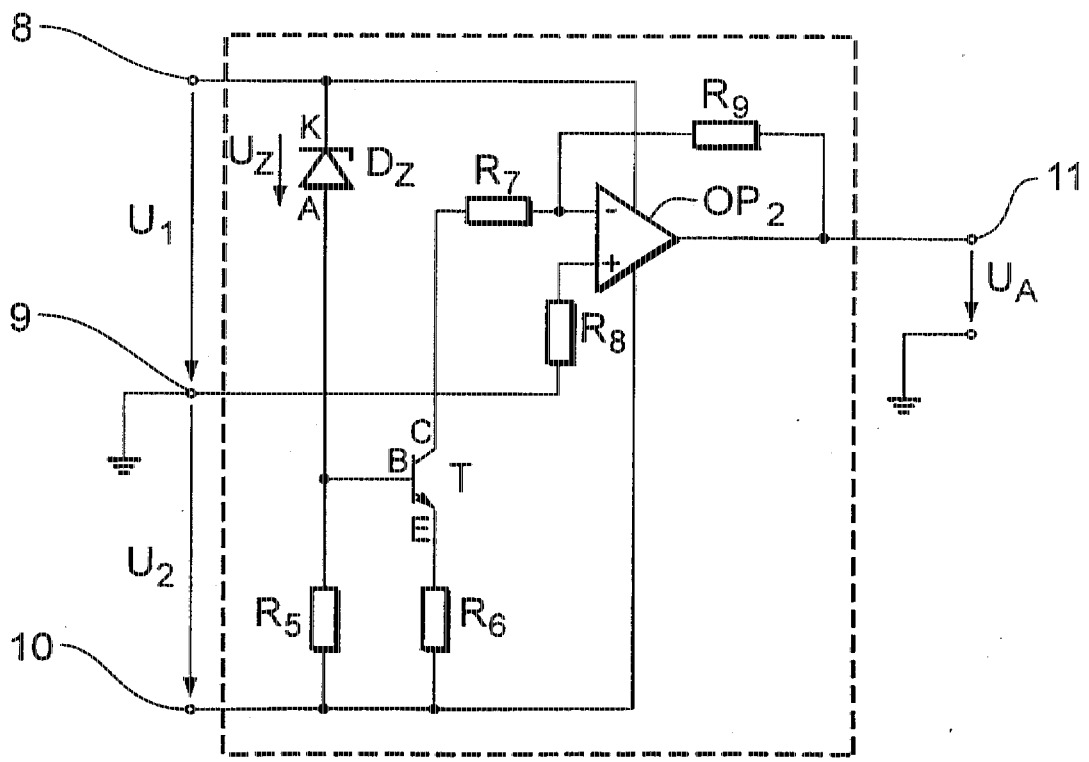

FIG. 3 shows a further embodiment of the measuring circuit 4 illustrated in FIG. 1, in detail as a circuit diagram.

Like the circuit shown in FIG. 2, the circuit, here, superposes the change in the first and second potentials relative to the reference potential.

At the input of the measuring circuit there is a level transducer comprising the zener diode $D_z$ and the resistor $R_5$. The level transducer forms the sum of the voltages $U_1$ and $U_2$ and reduces them by the constant voltage $U_z$ of the zener diode $D_z$. The voltage $U=U_1+U_2-U_z$, therefore, decreases at the resistor $R_5$. The total voltage drop of the battery can therefore be picked up at resistor $R_5$.

This voltage swing is fed to the operational amplifier OP2 via transistor T.

The operational amplifier OP2 amplifies the voltage swing and outputs a signal $U_A$ at out 11 which is approximately proportional to the total voltage swing.

By varying the ratios between resistors $R_9$ and $R_7$ the amplification factor of the operational amplifier OP2 may be adjusted and the level of the output voltage $U_A$ be adapted to the input of the threshold value member 5. The output voltage $U_A$ may be increased by increasing the quotient of $R_9$ and $R_7$ and correspondingly decreased by decreasing the quotient.

Figure 4:
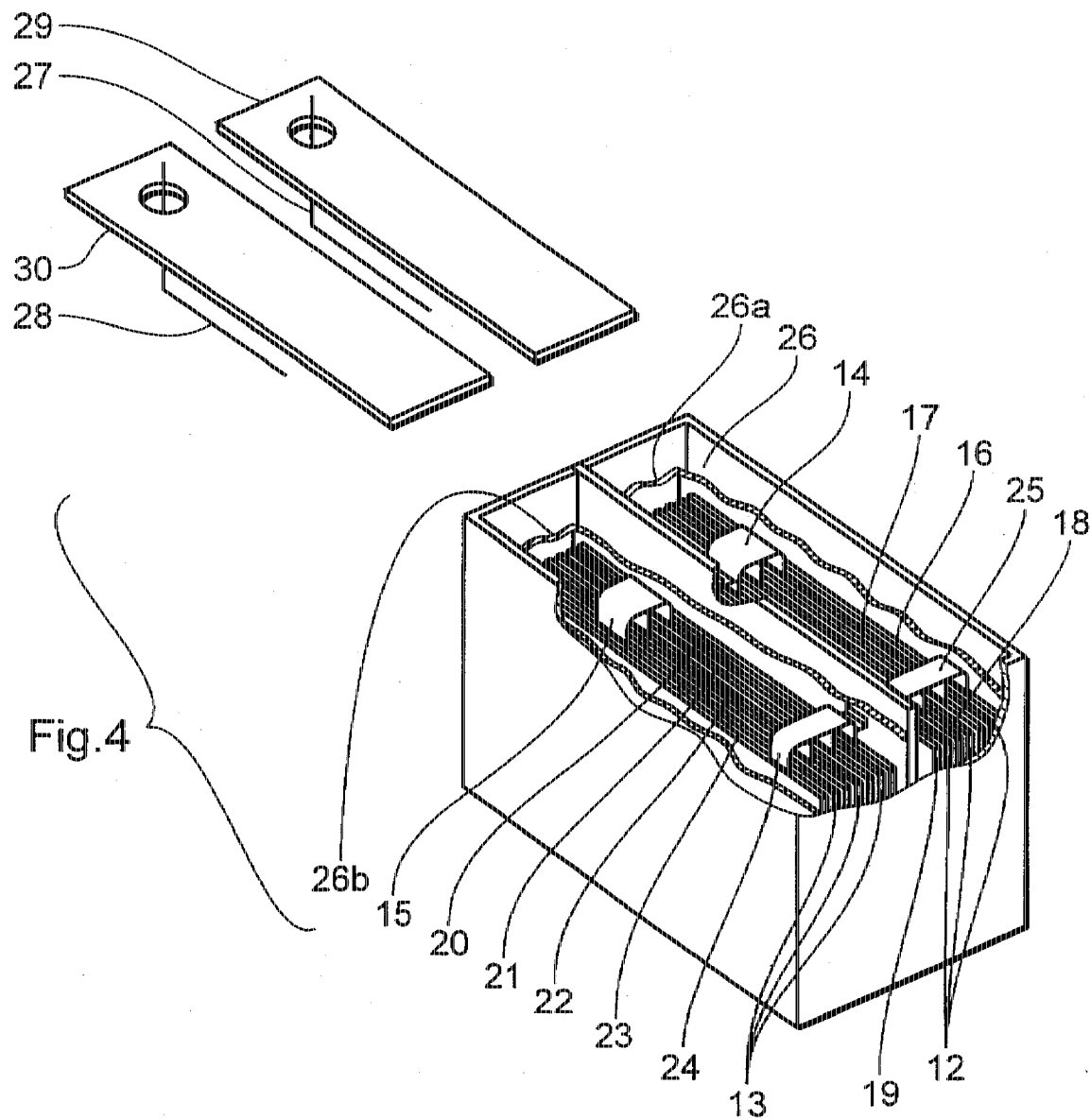

FIG. 4 shows an embodiment of the battery illustrated in FIG. 1 which has two cells and correspondingly two electrode packages each of which is accommodated in a compartment of a housing 15.

Each of the two electrode packages has three cathode plates 12 and 13 and four anode plates 16, 17, 18, 19 or 20, 21, 22, 23 as electrodes. The plates are of the same size and are arranged in parallel so that each cathode plate 12, 13 is, in each case, adjacent to two anode plates 16, 17, 18, 19, 20, 21, 22, 23. Electrode packages with four cathodes and five anodes etc. each are also feasible.

The cathode plates 12, 13 and the anode plates 16, 17, 18, 19, 20, 21, 22, 23 have a generally rectangular shape with a substantially uniform width across the depth and may be either flat or curved. This has the advantage that the electrode packages may be preassembled and, in this preassembled state, pushed into the compartments in the battery housing 26.

The cathode plates 12, 13 contain a mixture of $CrO_x$ with x between 2.5 and 2.7 or $MnO_2$ with $PbCrO_4$, $PbMoO_4$ or PbO or a mixture of $MnO_2$ with PbO, acetylene black, graphite and Teflon dispersion or components thereof.

The anode plates 16, 17, 18, 19, 20, 21, 22, 23 are preferably made of metal lithium.

The anode plates 16, 17, 18, 19 and 20, 21, 22, 23 forming part of an electrode package are each connected to one another by an anode connector 24 or 25 so as to be electrically conductive, while the cathode plates 12 and 13 forming part of an electrode package are each coupled to one another by a cathode connector 14 and 15 so as to be electrically conductive.

Here, the capacity of a cell is affected by the size of the surface of the electrode plates 12, 13, 16, 17, 18, 19, 20, 21, 22, 23 and the number of the plates connected in parallel.

The battery housing 26 mainly consists of a tub-like base, a dividing wall which separates two compartments in the housing and two covers 29, 30 which close the two compartments.

Both electrode packages are surrounded by a bag of non-conductive plastic material 26a, 26b and are thereby electrically insulated from the housing 26 and the dividing wall.

The housing, the covers 29, 30 and the dividing wall are made of an electrically conductive material and are coupled to one another so as to be electrically conductive. The dividing wall forms a connection between the two cells in which the cathode connector 14 of the first electrode package and the anode connector 24 of the second electrode package are connected to the dividing wall by means of spot welding. As the dividing wall is connected to the housing 15 so as to be electrically conductive, the voltage pick-up lies at earth potential. In this way the maximum voltage of the battery going to earth is limited to half the total voltage drop.

The anode connector 25 of the first electrode package and the cathode connector 15 of the second electrode package are insulated from one another and the housing 26 and are in the form of a pin passing through a glass passage provided in each of the covers 29, 30.

The whole battery is hermetically sealed.

Both compartments of the housing 26 are filled with an electrolyte, the level of filling being such that the electrode plates 12, 13, 16, 17, 18, 19, 20, 21, 22, 23 are fully covered. A mixture of propylene carbonate (PC), ethylene carbonate (EC), dimethoxyethane (DME) and $LiClO_4$ are used as electrolyte. The battery, however, can also be filled with other electrolytes (such as methylforimate, tetrahydrofuran) and other conducting salts (such as $LiAsF_6$, $LiPF_6$). As examples, the electrolyte may comprise 20 to 60% of ethylene carbonate (EC) and 5 to 20% of propylene carbonate (PC) and 30 to 70% of dimethoxyethane (DME), or $LiClO_4$ in a concentration of 1.0 to 1.5 $Mol \cdot l^{-1}$.

Figure 5:
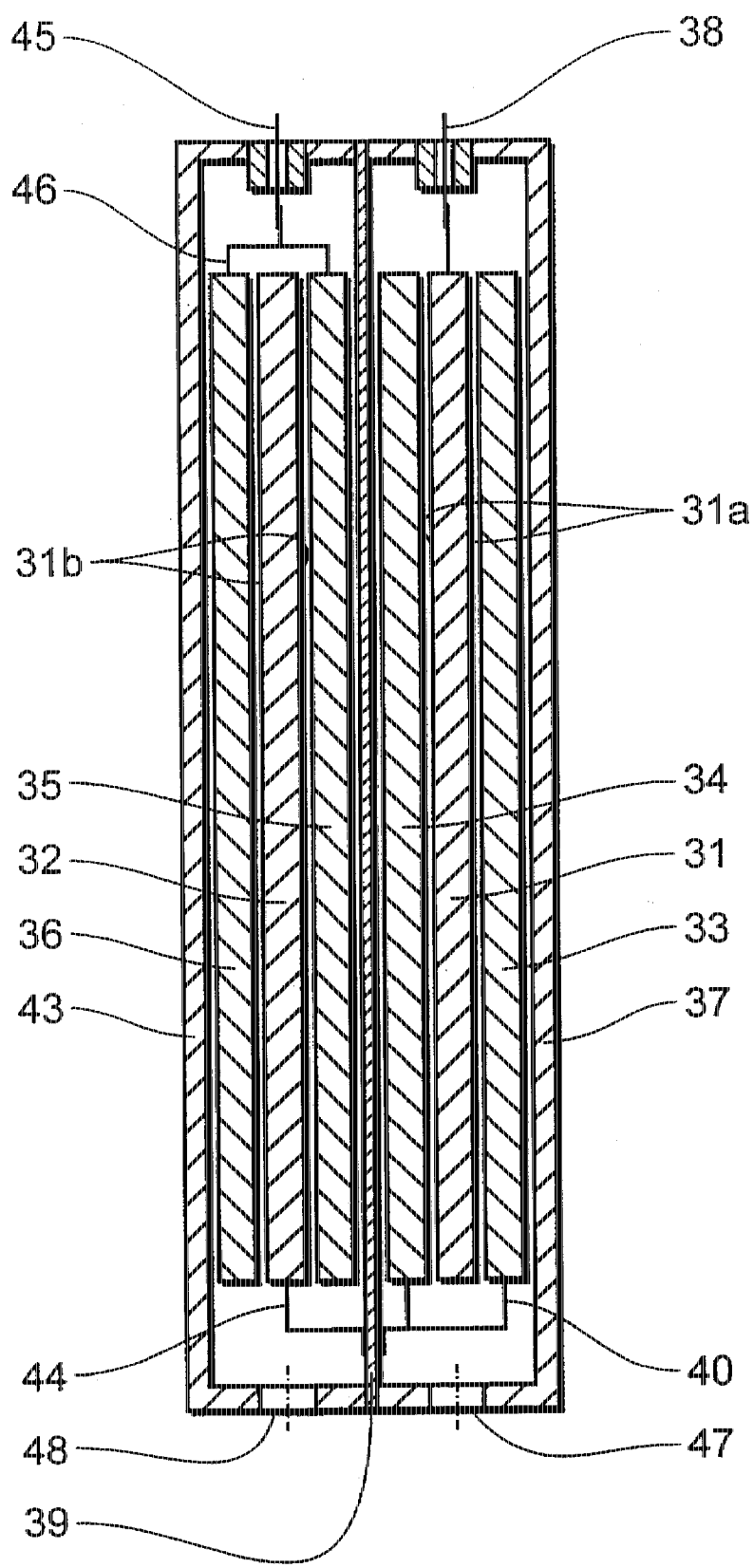

FIG. 5 shows a battery with two cells and correspondingly two electrode packages, each of which is accommodated within a compartment of a housing.

Each electrode package has one cathode plate 31 or 32 and two anode plates 33, 34 or 35, 36 as electrodes. They are each of the same size and the cathode plates 31 and 32 are arranged centrally between the anode plates 33, 34 or 35, 36 and are parallel thereto.

The spacing between the electrode plates 31, 32, 33, 34, 35, 36 is of the same magnitude as the thickness of the electrode plates 31, 32, 33, 34, 35, 36 which ensures that, on the one hand, the electrochemical processes taking place during the discharging operation function satisfactorily, and, on the other hand, the space available is used optimally.

The embodiment described here differs from that shown in FIG. 4 in the way it is encapsulated and, related thereto, in how the battery is assembled. The cathode and anode plates may be made of the same material, respectively, as described above. In FIGS. 4 and 5, the cathode plates may have their surfaces (e.g., surfaces 31a, 31b in FIG. 5) coated with a coating containing a binding agent and conduction additive. Preferably, the cathode plates have a porosity of 30 to 50%.

The housing consists mainly of two half shells 37 and 43 and one dividing wall 39.

Both the half shells 37 and 43 and the dividing wall 39 are made of an electrically conductive material and are coupled to one another so as to be electrically conductive. The dividing wall 39 forms an electrical connection between the two cells in which the anode connector 40 of the second electrode package and a contact 44 mounted on the cathode plate 32 of the first electrode package by means of spot welding is coupled to the dividing wall 39 so as to be electrically conductive, thereby forming a series connection of the two battery cells with one central voltage pick-up.

The construction of the housing in the form of two half shells 37, 43 has the advantage that, firstly, the electrode packages may be preassembled and secured to the dividing wall 39, and then the half shells 37, 43 may be placed on top of the circumferential wall 39 and sealed thereon. The welding operations for establishing contact between the dividing wall 39 and anode connector 40 or cathode plate 32, therefore, are simpler in terms of manufacturing technology.

A contact mounted on the cathode plate 31 of the second electrode package and the anode connector 46 of the first electrode package are insulated electrically and they pass through a glass passage 38 and 45.

Each half shell 37, 43 has, moreover, a closeable opening 47, 48 for introducing the electrolyte.

Preferably, the electrolyte consists of a mixture of propylene carbonate (PC), ethylene carbonate (EC) dimethoxyethane (DME) and $LiClO_4$, but other known combinations may also be used.

The invention is not restricted in its configuration to the preferred exemplary embodiments specified above. Rather, a number of variants which make use of the solution described are conceivable, even in the case of configurations of a fundamentally different type.

We claim:

1. Battery-operated, implantable medical device, comprising a battery, a measuring means for determining a state of charge of the battery by measuring a no-load voltage and an electric load the no-load voltage of the battery having an increased drop-off in a range in which a remaining residual energy is sufficient to maintain operation of the medical device for a minimum period of time required for carrying out a therapeutic process, wherein:

the battery includes a plurality of cells connected in a series circuit, a first voltage pick-up is arranged on a free anode of the battery for picking up a first potential and a second voltage pick-up is arranged on a free cathode of the battery for picking up a second potential, the electric load is electrically conductively coupled to the first and second voltage pick-ups to be energised by a total voltage drop across the battery, a third voltage pick-up is arranged on an electrode positioned between the free anode and free cathode series circuit in order to pick up a reference potential and to energise the measuring device with a symmetrical voltage supply, the measuring device includes a measuring circuit comprising at least one of a level transducer adding means, the measuring device being electrically conductively coupled at its inputs to the first and second voltage pick-ups for measuring the total voltage drop across the battery, the measuring device further includes a threshold value member with at least one threshold value coupled to an output of the measuring circuit for generating a battery condition signal, the measuring circuit and the threshold value member each has an input for a reference point which is electrically conductively coupled to the third voltage pick-up, and the measuring circuit and the threshold value member are each electrically conductively coupled to the first and second voltage pick-ups to be energised with a voltage in symmetry with the third voltage pick-up.

2. Battery-operated device according to claim 1, wherein the measuring circuit constitutes the adding means and includes four resistors ($R_1$, $R_2$, $R_3$, $R_4$) and one operational amplifier (OP) with a P-input (+), an N-input (−), an output and two voltage supply inputs, the first resistor ($R_1$) connects the N-input (−) of the operation amplifier (OP) with the first voltage pick-up, the second resistor ($R^2$) connects the N-input (−) of the operational amplifier (OP) with the output thereof to generate a feedback, the third resistance ($R_3$) couples the P-input (+) of the operational amplifier (OP) to the third voltage pick-up, the fourth resistance ($R_4$) couples the P-input (+) of the operational amplifier (OP) to the second voltage pick-up, the operational amplifier has voltage supply inputs coupled to the first and the second voltage pick-ups, and ratios of resistance values of the second ($R_2$) and the first ($R_1$) resistors and of the third ($R_3$) and the fourth ($R_4$) resistors are substantially equal.

3. Battery-operated device according to claim 1, wherein the measuring circuit includes an amplifier having output signal adapted to the threshold value member, and a level transducer for picking up a decrease in voltage swing across the battery and for adaptation to the amplifier, wherein the level transducer comprises a zener diode ($D_z$) and a first resistor ($R_5$), the zener diode having a cathode (K) coupled to the first voltage pick-up and an anode coupled to the second voltage pick-up through the first resistor ($R_5$), a transistor (T) having an emitter circuit for picking up the total decrease in voltage swing across the battery and for adaptation to the input of an amplifier the transistor having a base (B) connected to the anode (A) of the zener diode ($D_z$) and an emitter connected to the second voltage pick-up by a second resistor ($R_6$), the amplifier comprises third ($R_7$), fourth ($R_8$) and fifth ($R_9$) resistors and an operational amplifier (OP2) with an N-input (−), a P-input (+), an output and two voltage supply inputs, the N-input (−) of the operational amplifier (OP2) is connected to a collector (C) of the transistor (T) by the third resistor ($R_7$), the P-input (+) of the operational amplifier (OP2) is connected to the third voltage pick-up by the fourth resistor ($R_8$), the output of the operational amplifier (OP2) is connected to the N-input (−) by the fifth resistor ($R_9$) in order to achieve a feedback, and the voltage supply inputs of the operational amplifier (OP2) are connected to the first and second voltage pick-ups.

4. Battery-operated device according to claim 1, further including a housing connected to the third voltage pick-up so as to be electrically conductive.

5. Battery-operated device according to claim 1, wherein the measuring device includes a transmitter/receiver unit for an off-line or on-line transfer of the battery condition signal to a receiver unit positioned outside the device and/or for receiving an activation signal from a transmitter unit positioned outside the device.

6. Battery-operated device according to claim 1, the electric load includes a control unit to regulate a current consumption of the load depending on the state of the charge of the battery, the battery condition signal being applied to the input of the control unit.

7. Battery-operated device according to claim 1, wherein the battery has a housing which is hermetically sealed in an assembled state and has two cells which are electrically connected to form a series circuit and are spatially separated by a dividing wall, each cell has an electrode package comprised of anode plates and cathode plates which are alternatingly arranged next to one another, in each of the two cells the cathode plates are coupled to one another by a cathode connector and the anode plates are coupled to one another by an anode connector so as to be electrically conductive, the anode connector of the first cell is coupled to the first voltage pick-up and the cathode connector of the second cell is coupled to the second voltage pick-up so as to be electrically conductive, and the anode connector of the second cell and the cathode connector of the first cell are electrically conductively coupled to the dividing wall, the housing and the third voltage pickup.

8. Battery-operated device according to claim 7, wherein the electrode packages are contained in a bag comprised of plastic material so as to be insulated from the housing and the dividing wall.

9. Battery-operated device according to claim 7, wherein the housing includes two half shells.

10. Battery-operated device according to claim 7, wherein the cathode plates contain a mixture of one of $CrO_x$ with x between 2.5 and 2.7, and $CrO_x$ and $MnO_2$ with one of $PbCrO_4$, $PbMoO_4$, $PbO$ and a mixture of $MnO_2$ with $PbO$.

11. Battery-operated device according to claim 7, wherein the cathode plates have a surface with a coating which contains a binding agent and a conduction additive.

12. Battery-operated device according to claim 7, wherein the cathode plates have a porosity of 30 to 50%.

13. Battery-operated device according to claim 7, wherein the anode plates are comprised of lithium.

14. Battery-operated device according to claim 1, wherein the battery has an electrolyte which contains 20 to 60% of ethylene carbonate (EC) and 5 to 20% of propylene carbonate (PC) and 30 to 70% of dimethoxyethane (DME).

15. Battery-operated device according to claim 14, wherein the electrolyte contains $LiClO_4$ in a concentration of 1.0 to 1.5 $Mol \cdot l^{-1}$.

16. Battery-operated device according to claim 7, wherein the housing is comprised of CrNi-steel, molydenum, titanium or nickel.

* * * * *